(12) United States Patent
Kim et al.

(10) Patent No.: US 10,213,200 B2
(45) Date of Patent: Feb. 26, 2019

(54) TISSUE-CUTTING AND -SEALING FORCEPS

(71) Applicants: Denise Sujin Kim, Atlanta, GA (US);
Jacquelyn Borinski, Atlanta, GA (US);
Mohamad Ali Najia, Atlanta, GA (US);
Drew Padilla, Atlanta, GA (US)

(72) Inventors: Denise Sujin Kim, Atlanta, GA (US);
Jacquelyn Borinski, Atlanta, GA (US);
Andrew Kolpitcke, Atlanta, GA (US);
Mohamad Ali Najia, Atlanta, GA (US);
Drew Padilla, Atlanta, GA (US)

(73) Assignee: Emory University, Atlanta, GA (US)

(*) Notice: Subject to any disclaimer, the term of this patent is extended or adjusted under 35 U.S.C. 154(b) by 425 days.

(21) Appl. No.: 14/959,184

(22) Filed: Dec. 4, 2015

(65) Prior Publication Data
US 2016/0157876 A1    Jun. 9, 2016

Related U.S. Application Data

(60) Provisional application No. 62/087,693, filed on Dec. 4, 2014.

(51) Int. Cl.
| A61B 17/072 | (2006.01) |
| A61B 17/30 | (2006.01) |
| A61B 17/00 | (2006.01) |
| A61B 17/32 | (2006.01) |

(52) U.S. Cl.
CPC ............ *A61B 17/072* (2013.01); *A61B 17/30* (2013.01); *A61B 2017/00004* (2013.01); *A61B 2017/00792* (2013.01); *A61B 2017/07278* (2013.01); *A61B 2017/320052* (2013.01)

(58) Field of Classification Search
CPC .................. A61B 17/29; A61B 17/072; A61B 2017/2926; A61B 2017/00367
USPC .............. 227/178.1, 19, 179.1; 606/151, 157
See application file for complete search history.

(56) References Cited

U.S. PATENT DOCUMENTS

| 4,930,674 A * | 6/1990 | Barak ................... A61B 17/072 227/179.1 |
| 8,876,859 B2 * | 11/2014 | Buehler ............. A61B 17/0206 606/210 |
| 2010/0331880 A1 * | 12/2010 | Stopek ............... A61B 17/0644 606/219 |
| 2011/0036891 A1 * | 2/2011 | Zemlok ............ A61B 17/07207 227/176.1 |

* cited by examiner

*Primary Examiner* — Nathaniel Chukwurah
(74) *Attorney, Agent, or Firm* — Troutman Sanders LLP; Ryan A. Schneider (57) ABSTRACT

Implementations of the disclosed technology include a forcipate surgical instrument including a channel at the working end for guiding a scalpel blade during tissue resection. In some implementations, the forceps may also include a scalpel-driven stapling mechanism for sealing the tissue simultaneously with resection via a single scalpel motion.

16 Claims, 11 Drawing Sheets

PRIOR ART

TISSUE-CUTTING AND -SEALING FORCEPS

CROSS-REFERENCE TO RELATED APPLICATIONS

This Application claims priority and the benefit under 35 U.S.C. § 119(e) of U.S. Provisional Patent Application No. 62/087,693, filed 4 Dec. 2014, of which the entire contents and substance are hereby incorporated by reference as if fully set forth below.

BACKGROUND

Drooping eyelids, or ptosis, caused by the elongation of the inner eyelid Müller's muscle is a functional, age-associated condition that severely obstructs and blurs the field of vision of over five million Americans. Of the approximately 200,000 ptosis repair surgeries performed annually in the United States, up to 25% of patients require additional corrective surgeries due to surgical complications.

In the established surgical paradigm, oculoplastic surgeons use conventional surgical forceps to grasp the excess Müller's muscle while suturing the tissue directly below the clamp and resecting the muscle in between the sutures and clamp. Complications may arise when surgeons accidently cut the sutures applied on the inner eyelid when resecting the excess Müller's muscle, ultimately resulting in an abnormally short eyelid for the patient.

A significant contributing factor to the high occurrence of complications during ptosis repair is the potential to mistakenly sever one's sutures while excising Mueller's muscle with a #15 blade beneath conventional surgical forceps during the procedure. Moreover, conventional surgical forceps are often unhelpful in establishing a precise determination of an appropriate amount of tissue to resect, leading to inconsistent results.

Alternative tissue sealing solutions exist to suturing, such as surgical stapling devices. However, oculoplastic surgeons have been resistant to adoption of stapling solutions as conventional stapling devices are not adapted to the sensitive eyelid tissue anatomy, utilize abrasive staples, and do not provide fine control of crafting the eyelid contour.

SUMMARY

Some or all of the above or additional needs may be addressed by certain implementations of the disclosed technology. Certain implementations include a forceps having a channel at the working end for guiding a scalpel blade during tissue resection. In some implementations, the forceps may further include a scalpel-driven stapling mechanism, supplanting the need for the dexterous labor of suturing. The stapling mechanism may integrate with the channel, enabling tissue sealing to be performed simultaneously with resection via a single scalpel motion. In another implementation, the forceps may have linear graduations for helping precisely determine an appropriate amount of tissue to be resected. These and other features may lessen the training time required to become proficient in ptosis repair and enhance the ability of the surgeon to adapt to specific patients, thereby ensuring a safer surgery with fewer complications and less uncertainty of the cosmetic outcome.

According to an example implementation, a forcipate surgical instrument is provided. The forcipate surgical instrument may include an instrument body having a proximal end, an intermediate handle portion, and a working portion at a distal end. The instrument body may include first and second mutually opposed elongate arms. The arms may be hingedly secured together at the proximal end and thereby compressible toward each other and decompressible away from each other to respectively close and open a grasping assembly at the distal end.

The grasping assembly may have first and second elongate jaws, each jaw extending from a respective arm at the distal end. The jaws may be disposed substantially orthogonal to the arms or handle portion. The jaws may be adapted to grasp tissue therebetween when the arms are compressed.

The grasping assembly may be adapted to receive a scalpel blade inserted and slid along a channel running lengthwise through one or both jaws, in order to cut the tissue grasped therebetween when the grasping assembly is in a closed position.

According to an example implementation, a method of performing ptosis surgery is provided. The method may be performed using the forcipate surgical instrument described above, or certain other implementations described later herein. The method may include everting an upper eyelid of a patient to expose the patient's Müller's muscle. The method may further include positioning the forcipate surgical instrument such that the first and second jaws encompass a target region of the Müller's muscle to be resected. The method may yet further include compressing the arms of the forcipate surgical instrument in order to close the grasping assembly on the target region. The method may also include sealing the patient's Müller's muscle below the forcipate surgical instrument with a sealing agent. The sealing agent can include staples, sutures, adhesives, or other materials used to seal tissue in a medical procedure. The method may further include inserting a scalpel blade into an end of the channel and sliding the scalpel blade along the length of the channel in order to resect the target region.

According to an example implementation, a forceps is provided. The forceps may include a grasping assembly at a working portion of the forceps. The grasping assembly may have mutually opposed elongate jaws. Each jaw may be disposed substantially orthogonal to a handle portion or arms of the forceps. The grasping assembly may be adapted to receive a scalpel blade inserted and slid along a channel running lengthwise through at least one of the first and second jaws in order to cut the tissue grasped therebetween when the grasping assembly is in a closed position.

The forceps may further include a stapling assembly secured to at least one of the first and second jaws. The stapling assembly may comprise a cartridge for bio-compatible staples and a scalpel-driven mechanism to deposit the bio-compatible staples into the tissue when the scalpel blade is being slid along the channel. The bio-compatible staples may be deposited in one or more rows substantially parallel to the channel and on a side of the channel opposite the handle portion.

The forceps may further include a locking assembly disposed on the handle portion. The locking assembly may be operable to lock the grasping assembly in a closed position when engaged.

According to an example implementation, a method of performing ptosis surgery is provided. The method may be performed using the forceps described above, or certain other implementations described later herein. The method may include everting an upper eyelid of a patient to expose the patient's Müller's muscle. The method may further include positioning the forceps such that the first and second jaws encompass a target region of the Müller's muscle to be resected. The target region may be determined based on linear graduations or other markings on the forceps.

The method may yet further include compressing the arms of the forceps in order to close the grasping assembly on the target region. The method may also include engaging the locking assembly to lock the grasping assembly in the closed position. The method may further include inserting a scalpel blade into an end of the channel and sliding the scalpel blade along the length of the channel in order to staple and resect the Müller's muscle simultaneously through a same scalpel motion.

Other implementations, features, and aspects of the disclosed technology are described in detail herein and may be considered a part of the claimed technology. Such implementations, features, and aspects may be understood with reference to the following detailed description, accompanying drawings, and claims.

BRIEF DESCRIPTION OF THE FIGURES

Reference will now be made to the accompanying figures and flow diagrams, which are not necessarily drawn to scale, and wherein.

DETAILED DESCRIPTION

To enable surgeons to more safely and accurately resect and seal fine eyelid tissue and mitigate complications due to error, the present disclosure introduces a novel surgical clamp and corresponding surgical procedure to replace current tissue resection sealing techniques. In some implementations, custom-designed PLA/PGA bioabsorbable staples may be integrated into the clamp within disposable staple cartridges. Using a standard surgical scalpel to drive the stapling mechanism, a surgeon may quickly to resect the excess Müller's muscle and seal the incision with a single scalpel motion. Accordingly, certain implementations of the disclosed technology may transform ptosis repair surgery into a rapid office-based procedure, improve cosmetic outcomes, and establish a safer surgical paradigm.

Throughout this disclosure, certain implementations are described by way of example in relation to resecting and/or sealing a patient's Müller's muscle during ptosis repair. However, implementations of the disclosed technology are not so limited, and may be suitable in ENT, gastrointestinal, and other types of surgeries requiring the resection and sealing of fine tissue.

Some implementations of the disclosed technology will be described more fully hereinafter with reference to the accompanying drawings. The disclosed technology may, however, be embodied in many different forms and should not be construed as limited to the implementations set forth therein.

In the following description, numerous specific details are set forth. However, it is to be understood that implementations of the disclosed technology may be practiced without these specific details. In other instances, well-known methods, structures, and techniques have not been shown in detail in order not to obscure an understanding of this description. References to "one implementation," "an implementation," "example implementation," "some implementations," "certain implementations," "various implementations," etc., indicate that the implementation(s) of the disclosed technology so described may include a particular feature, structure, or characteristic, but not every implementation necessarily includes the particular feature, structure, or characteristic. Further, repeated use of the phrase "in one implementation" does not necessarily refer to the same implementation, although it may.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

Unless otherwise specified, the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

In some instances, various implementations of the disclosed technology may be referred to as "forcipate surgical instruments," "forceps," "clamps," or "tweezers," or the like. One of skill in the art will appreciate in which instances these terms may be interchangeable or alternative. Moreover, in some instances, "sealing forceps" may refer to certain implementations incorporating the resection channel 465 for receiving a scalpel 300, while "sealing and resecting forceps" may refer to certain implementations incorporating both the resecting channel and the scalpel-driven stapling mechanism 700.

Various devices and methods may be utilized for improving resecting and sealing fine tissue, and will now be described with reference to the accompanying figures.

Figure 1A:
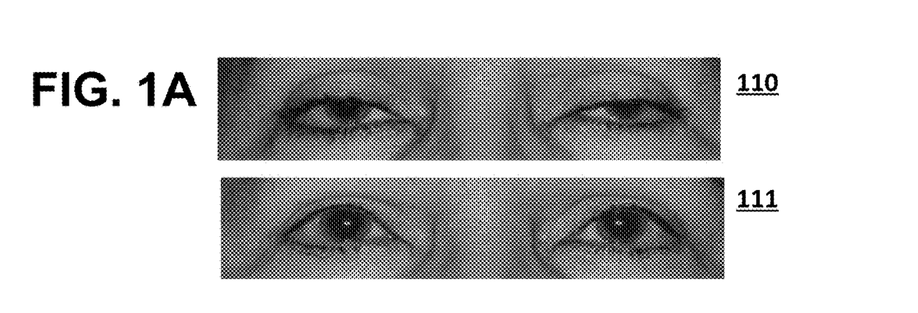
FIG. 1A depicts photos of a patient before 110 and after 111 ptosis repair surgery, according to an example implementation.
Figure 1B:
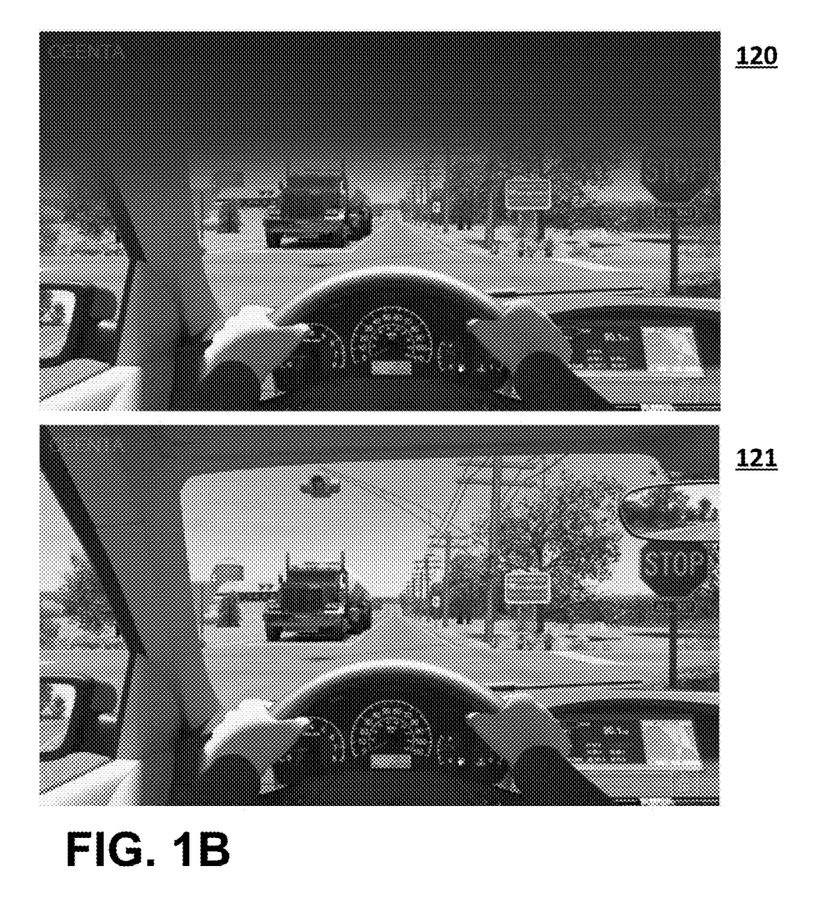
FIG. 1B depicts illustrations of patient's visual field before 120 and after 121 ptosis repair surgery, according to an example implementation.

Acquired ptosis is a condition in which the levator or Müller's eyelid muscle is weakened, elongated, or dehisced, causing the eyelid to droop. FIG. 1A depicts photos of a patient before 110 and after 111 ptosis repair surgery, according to an example implementation. Ptosis is responsible for obstructing the field of vision and impairing the daily activities of more than 75,000 Americans each year. As shown in FIG. 1B, commons tasks like driving or walking may become much harder and unsafe with ptosis. Moreover, more than 80% ptosis patients are over sixty years old and thus especially prone to fall-related injuries. Ptosis also frequently leads to headaches when the patient compensates for the lack of eyelid muscle function by activating the frontalis muscle to elevate the brows and lid margins.

Figure 2:
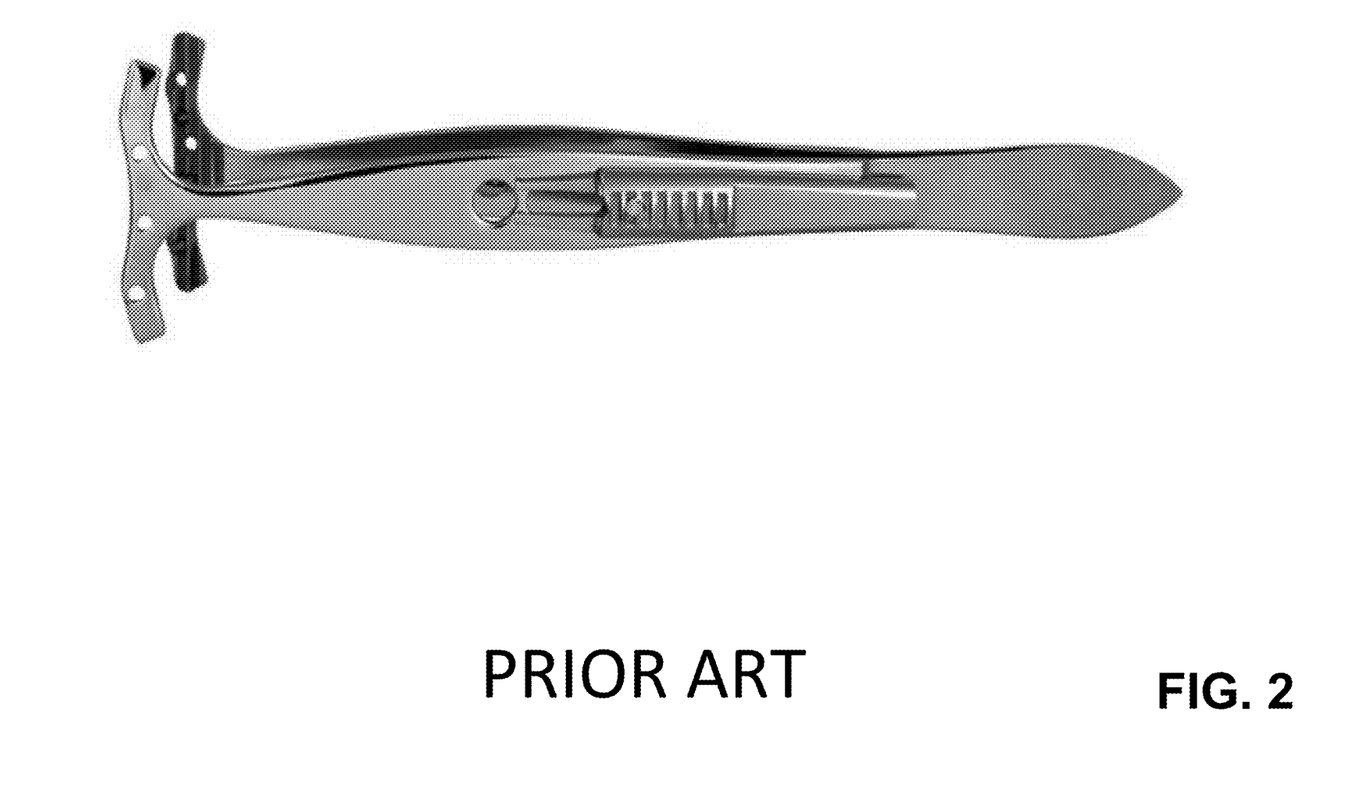
FIG. 2 depicts an illustration of a conventional clamp 200 used in ptosis repair surgery, according to an example implementation.
Figure 3:
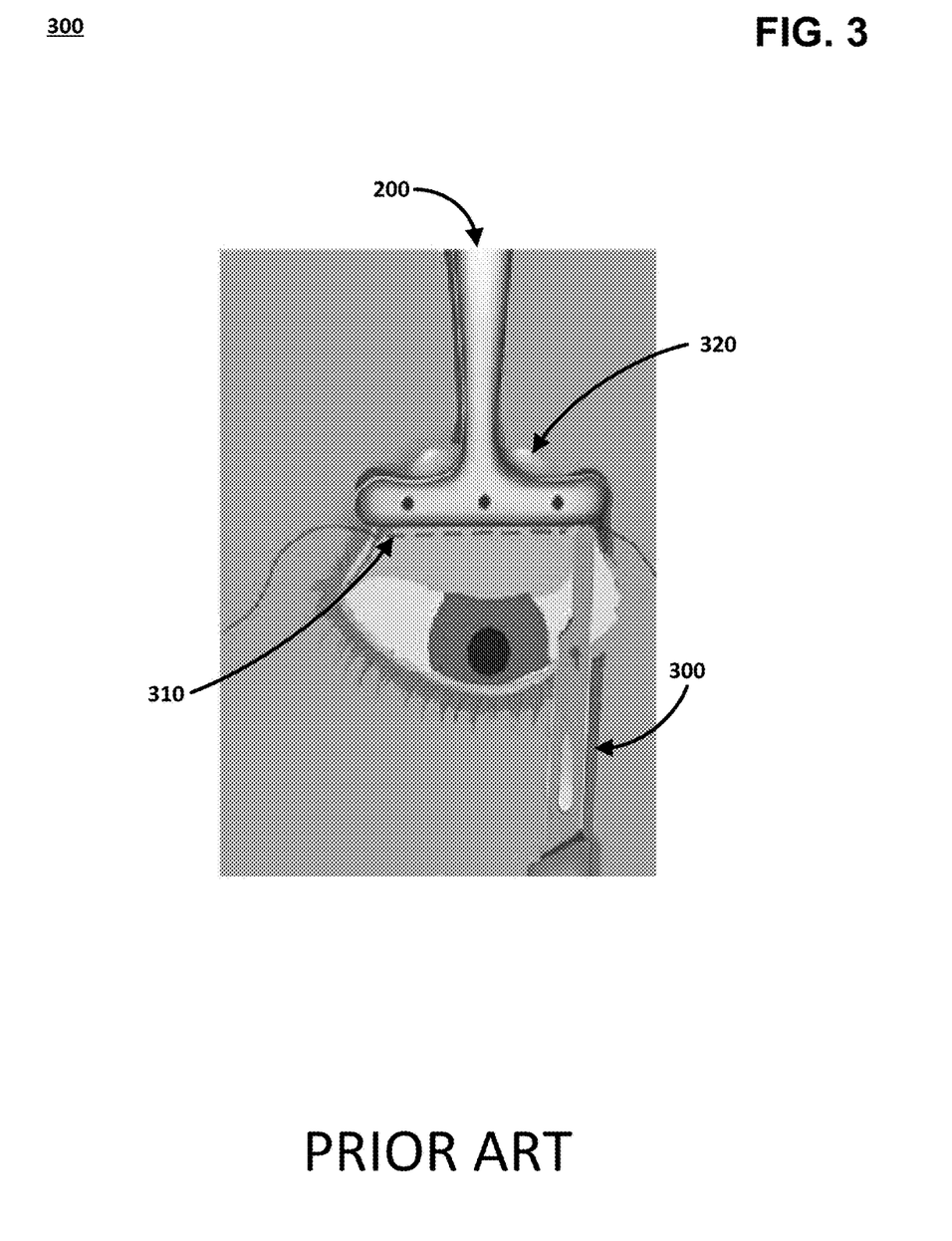
FIG. 3 depicts an illustration 300 of a conventional ptosis repair procedure, according to an example implementation.

FIG. 3 depicts an illustration 300 of a conventional ptosis repair procedure, according to an example implementation. In the established surgical treatment paradigm, oculoplastic surgeons may use surgical forceps such as the clamp 200 shown in FIG. 2 to grasp and immobilize the excess Müller's muscle 320 while suturing the tissue directly below the forceps, and resecting the muscle in between the sutures and the forceps with a scalpel 300.

Oculoplastic surgeons often accidently cut the sutures 310 applied on the inner eyelid when resecting the excess Müller's muscle 320. Consequently, additional tissue must be resected beyond that originally intended, potentially leaving the patient with an abnormally short eyelid. Of the approximately 200,000 ptosis repair surgeries performed annually in the United States, over 25% of cases require additional corrective surgeries due to the aforementioned issue, resulting in one of highest post-operative repair rates.

From observing conventional ptosis repair surgeries, the inventive team identified that oculoplastic surgeons require significant fine motor control when suturing and resecting eyelid tissue. The considerable manual dexterity required is a root cause of surgeons accidently compromising the integrity of the sealing agent during tissue resection. With patient safety and simplification of the surgical workflow in mind, certain implementations of the disclosed technology were engineered to provide controlled resection of the excess Müller's muscle. Some implementations may also facilitate sealing of the incision, for example, with proprietary bioabsorbable staples.

According to certain implementations, simultaneous resecting and sealing may be accomplished using a standard surgical scalpel to drive a stapling mechanism in a guided framework in the jaws of the forceps. The scalpel-driven stapling mechanism described herein is unique to the disclosed technology and may transform ptosis repair from a 45-minute operating room surgery into a 5-minute office-based procedure. Some implementations may provide a self-contained solution to enable safe and precise resection of eyelid tissue across various degrees of eyelid drooping. Accordingly, surgeons and patients may be offered peace of mind in the operative outcome, a higher standard of care, and a reduced risk of surgical complications.

Conventional Procedure

The steps involved in conventional ptosis repair provide insight into the opportunity for a device that simultaneously cuts and seals Müller's muscle 320. Returning to the conventional ptosis repair procedure, as shown in FIG. 3, first the surgeon everts the upper eyelid using a retractor, then measures and marks the region of Müller's muscle to be resected with calipers. A Putterman clamp 200, as shown in FIG. 2, is placed on the marked region of Müller's muscle 320. The clamp is then closed and locked around the tissue that will be resected. A suture 310, either removable or absorbable, is passed back and forth approximately 1 mm beneath the clamp, running the length of the eyelid.

If the spacing or alignment of the two pieces of muscle that are being sewn together is inconsistent, the cosmetic result of the procedure may be adversely affected. Additionally, less experienced surgeons may prefer to have an assistant holding the Putterman clamp 200, increasing the number of professional required to perform the procedure.

After the sutures 310 are in place, typically a 15-blade scalpel 300 is used to excise the tissue secured by the clamp by cutting between the bottom of the clamp and the row of sutures. While cutting, the surgeon must manually ensure that they do not accidentally cut any of the sutures with the scalpel blade.

Figure 7:
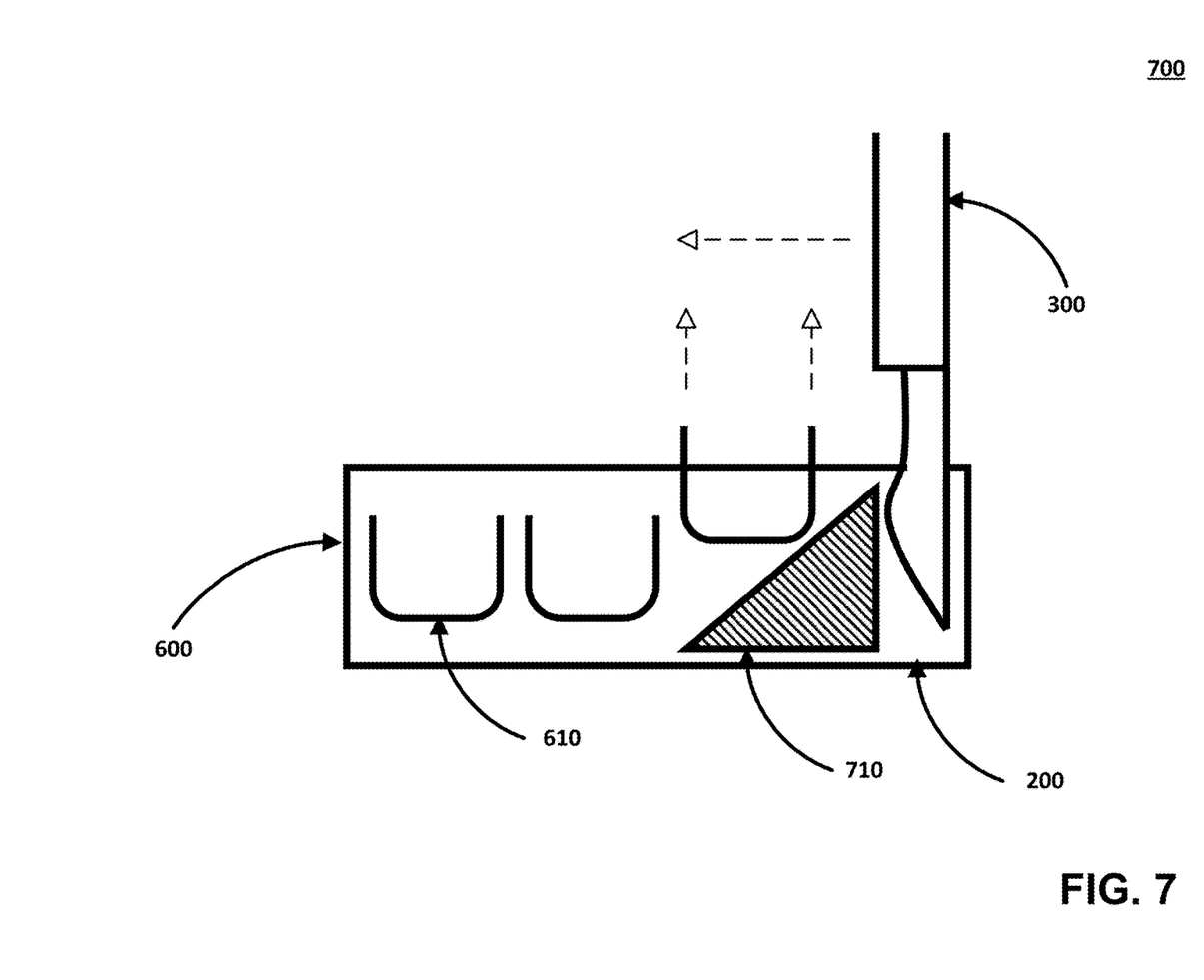
FIG. 7 depicts an illustration of the scalpel-driven stapling mechanism 700, according to an example implementation.

In contrast, certain implementations of the disclosed technology may provide controlled resection of the excess Müller's muscle by guiding the scalpel blade 300 along a fixed path isolated from the sutures. Some implementations may further eliminate the need for sutures by providing an alternative tissue sealing solution, for example, scalpel-driven stapling mechanism 700.

Example Device and Method

Figure 4:
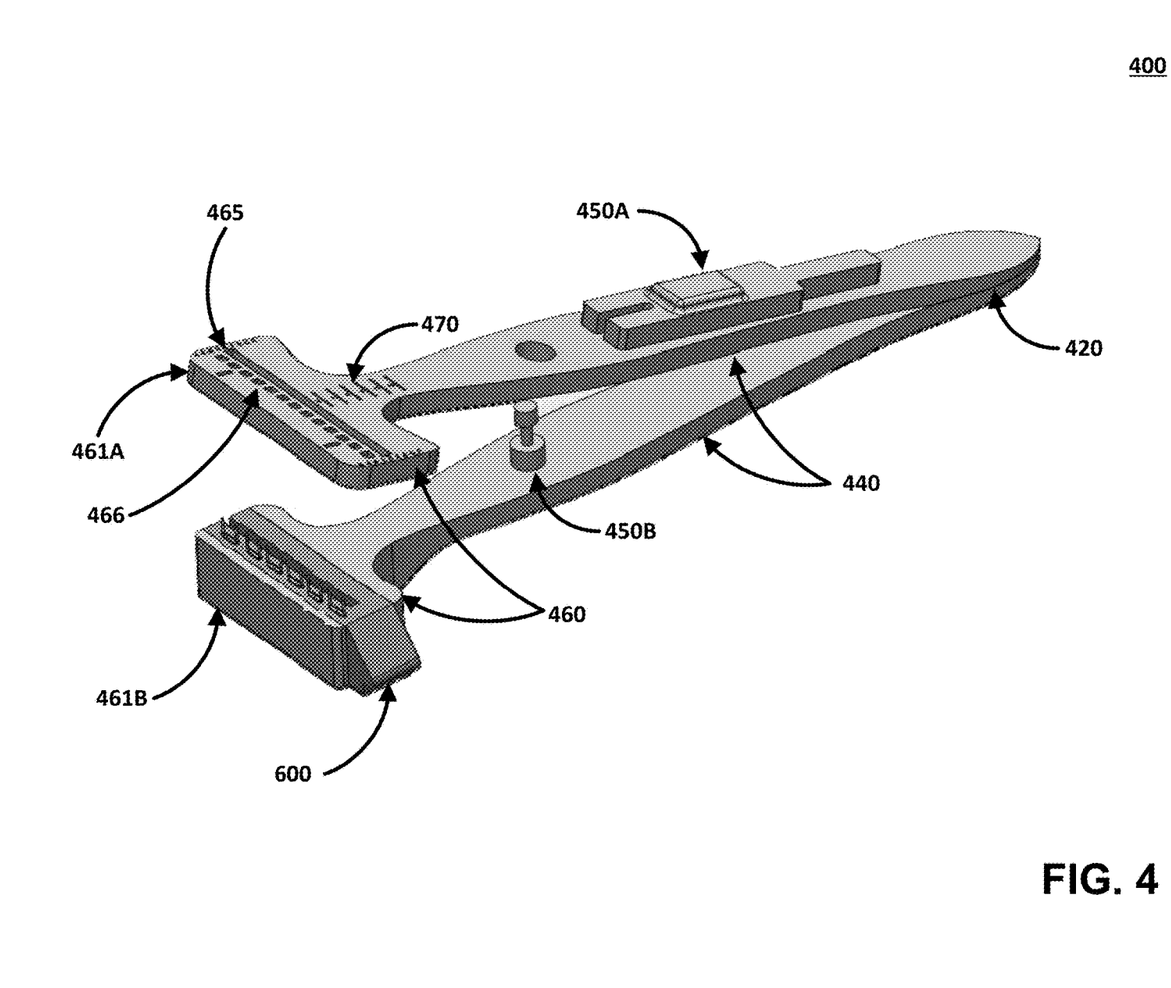
FIG. 4 depicts an illustration of the resecting and sealing forceps 400, according to an example implementation.

FIG. 4 depicts an illustration of the resecting and sealing forceps 400, according to an example implementation. In some implementations, the forceps may be thumb forceps, or "tweezer" style. Accordingly, the arms of the forceps may be hingedly secured near or at a proximal end 420 of the instrument body, with a working portion 460 at the distal end, and a handle portion 440 in between, as shown in FIG. 4. Alternatively, the forceps may be hinged between the handle portion and working portion, for example, with the handle portion having a "scissors"-style grip.

The arms of the forceps may be compressible towards each other and decompressible away from each other to respectively close and open a grasping assembly at the distal end. The term "decompressible" can include both an active opening of the forceps, or a passive relaxing away due to the inherent structure of the forcep. Preferably, decompressible can be relaxing away. The grasping assembly may comprise jaws 461A-B for grasping and immobilizing tissue when the arms are compressed. The jaws may have teeth or other features for providing improved grip. Each jaw may be elongate, extending from and being disposed substantially orthogonal to the arms or handle portion, as shown in FIG. 4. The jaws may also be connected to the instrument body at the center of each jaw, as shown in FIG. 4. Alternatively, the jaws may be disposed at another angle or connected to the instrument body on a side of the jaws. Other forceps configurations will be apparent to one of skill in the art and are considered within the scope of this disclosure.

Figure 5:
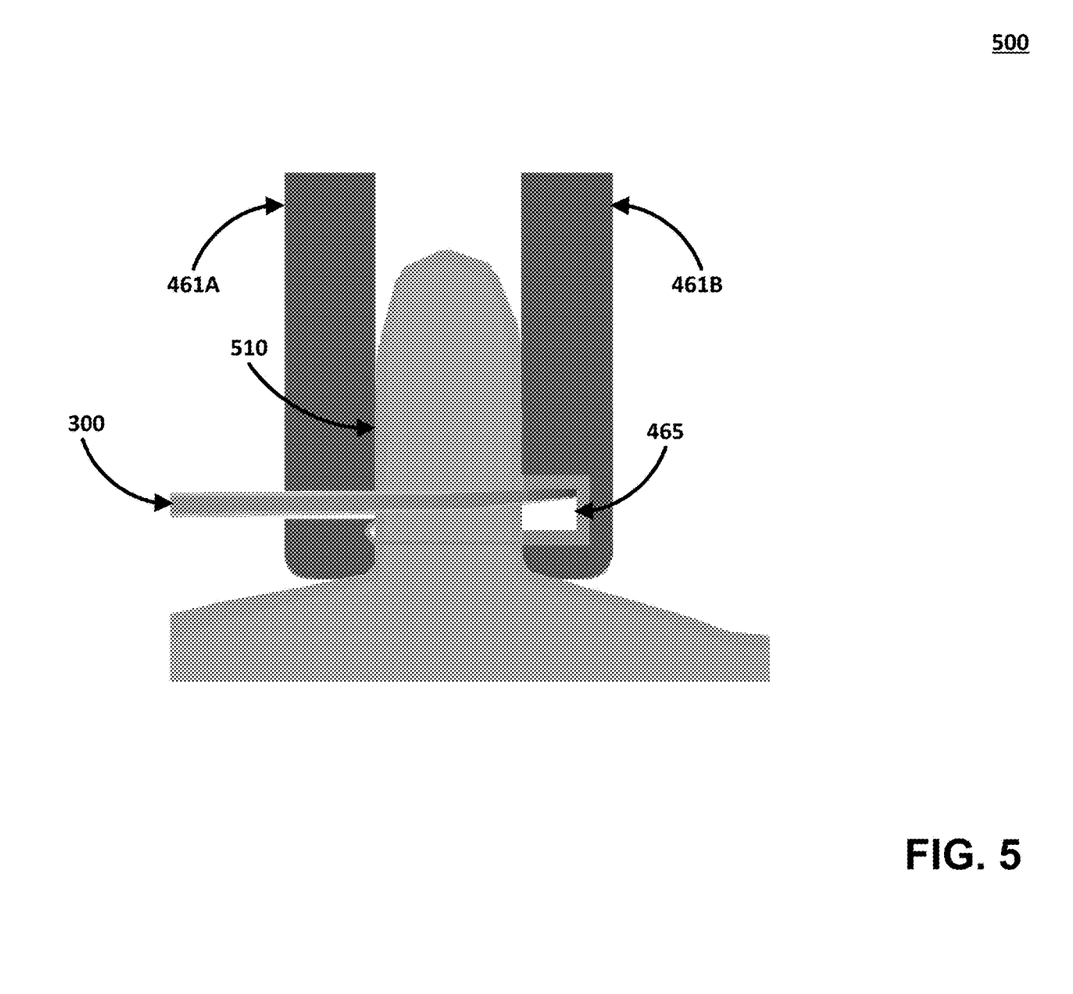
FIG. 5 depicts an illustration 500 of tissue 510 being resected by a scalpel 300 slid through the channel 465 of the resecting forceps, according to an example implementation.

According to certain implementations, the grasping assembly may be adapted to receive a scalpel blade inserted or slid along a resection channel 465 running lengthwise through at least one of the jaws 461A-B. Accordingly, the surgeon's scalpel 300 may be guided along a precise cutting path when resecting tissue secured between the jaws. FIG. 5 depicts an illustration 500 of tissue 510 being resected by a scalpel 300 slid through the channel 465 of the resecting forceps, according to an example implementation.

Figure 8:
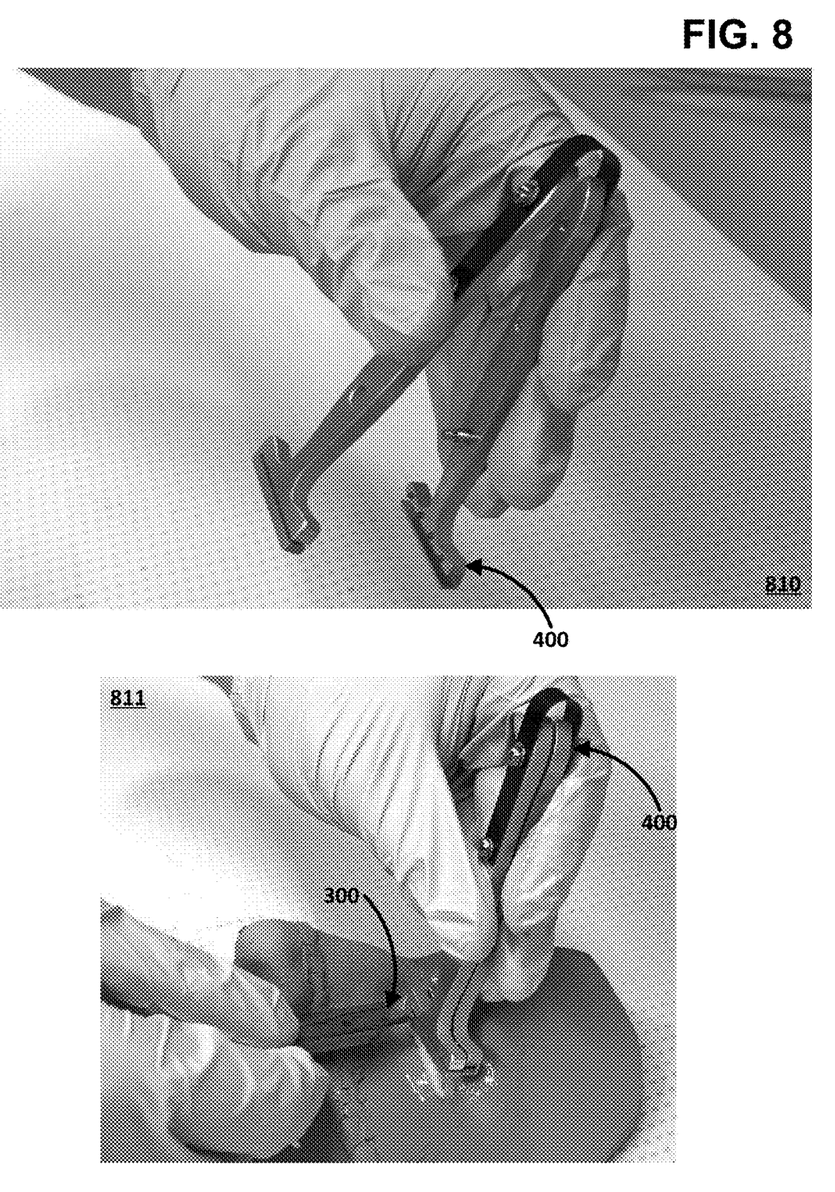
FIG. 8 depicts illustrations 810 and 811 of resecting tissue using resecting forceps 400, according to an example implementation.

In some implementations, the channel 465 may be closed at both ends, as shown in the forceps 400 of FIG. 4, or open at one end as shown in the forceps 400 of FIG. 8. In some implementations, an open end of the channel may be positioned opposite or away from the nose of the patient during ptosis repair. Accordingly, the scalpel 300 may be slid through the channel and away from the patients' nose to reduce risk of complications. In such implementations, eye-specific (or mirror-image) forceps may be used for left and right patient eyes. In another implementation, a same forcipate instrument may be used for repair of both patient eyes.

Figure 10:
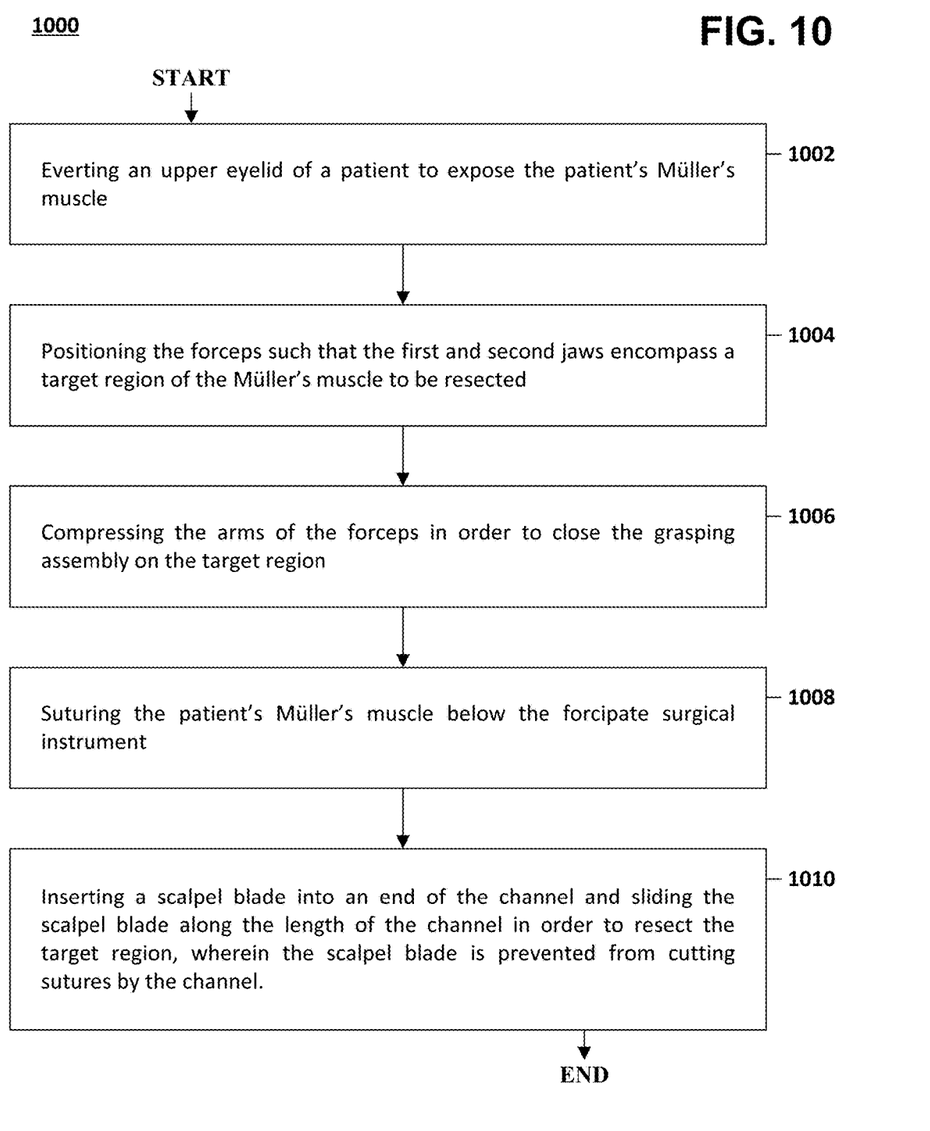
FIG. 10 is a flow diagram of a method 1000 for performing ptosis repair using the resecting forceps, according to an example implementation.

FIG. 10 is a flow diagram of a method 1000 for performing ptosis repair using the resecting forceps, according to an example implementation. As shown in FIG. 10, the method 1000 starts in block 1002, and, according to an example implementation, includes everting an upper eyelid of a patient to expose the patient's Müller's muscle. In block 1004, the method 1000 includes positioning the forceps such that the first and second jaws encompass a target region of the Müller's muscle to be resected. In block 1006, the method 1000 includes compressing the arms of the forceps in order to close the grasping assembly on the target region. In block 1008, the method 1000 includes suturing the patient's Müller's muscle below the forcipate surgical instrument. In block 1010, the method 1000 includes inserting a scalpel blade into an end of the channel and sliding the scalpel blade along the length of the channel in order to resect the target region, wherein the scalpel blade is prevented from cutting sutures by the channel.

Figure 6:
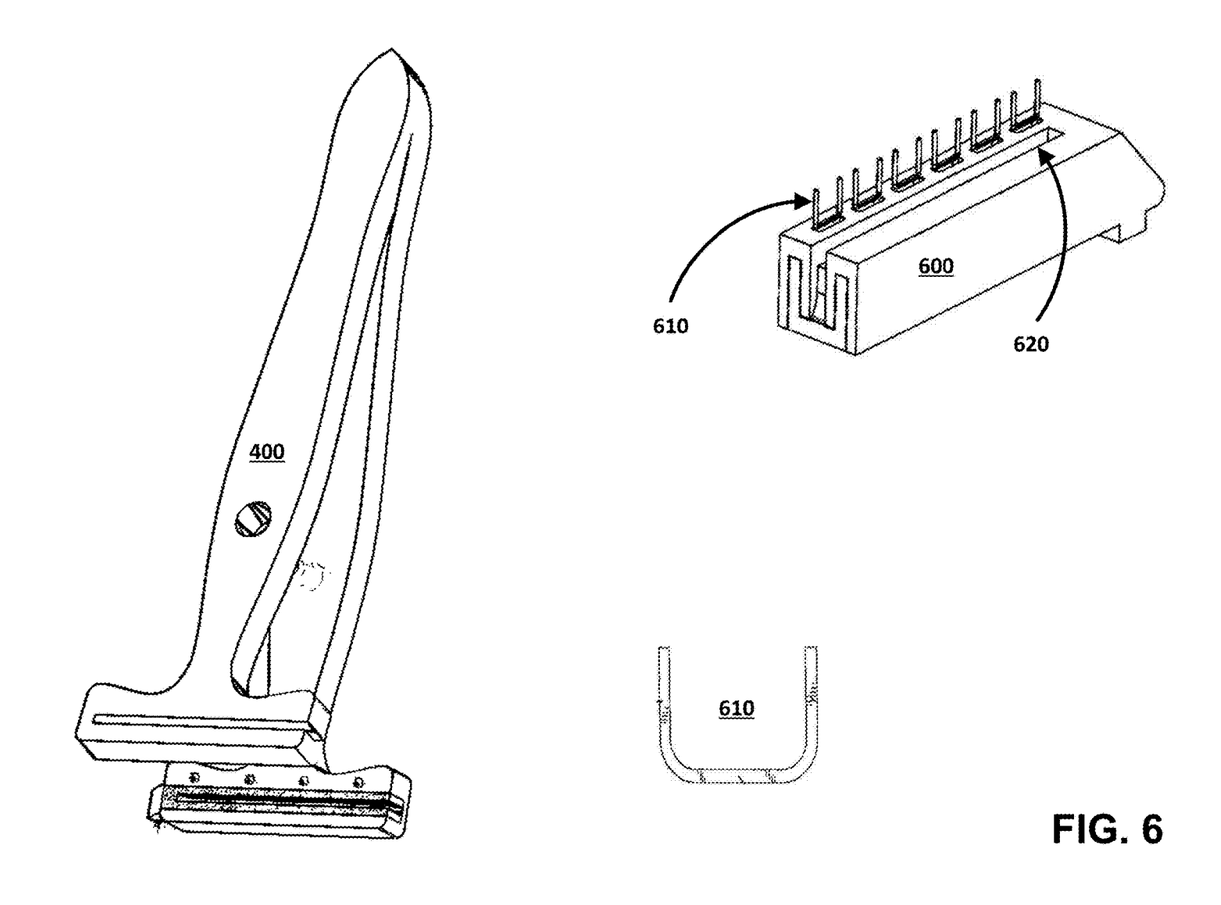
FIG. 6 depicts illustrations of the resecting and sealing forceps 400, staple cartridge 600, and staples 610, according to an example implementation.

According to certain implementations, a stapling assembly may be secured to, or incorporated in, at least one of the jaws 461A-B. The stapling assembly may be adapted to seal tissue grasped between the jaws when the forceps 400 is in a closed position. As shown in FIG. 6, the stapling assembling may include a cartridge 600 containing staples 610 for sealing tissue. In some implementations, the cartridge 600 may include a scalpel-driven stapling mechanism for depositing staples into the tissue. For example, the cartridge may have a knife slot 620 or other cavity that aligns with the resection channel 465 to receive the scalpel 300. FIG. 7 depicts an illustration of the scalpel-driven stapling mechanism 700, according to an example implementation. As shown in FIG. 7, the scalpel 300, when inserted into the cartridge's knife slot, may contact an ABS wedge 710 within the cartridge. When the scalpel is slid along the channel, the wedge may be displaced by the scalpel blade, thereby directing staples 610 from the staple cartridge into the tissue. The staples may be secured and formed into the tissue by micro-anvils 466 or the like on the opposite inner jaw of the forceps 400. Thus, with a same scalpel motion, tissue grasped between the jaws may be simultaneously resected and sealed.

According to certain implementations, the staples 610 may be deposited in one or more rows substantially parallel to the resection channel 465 and on a side of the channel opposite the handle portion of the forceps. The placement of the channel permits the excess Müller's muscle to be cut a controlled distance above the staples. When the jaws 461A-B of the forceps 400 are opened, the staples may become recessed into the tissue, preventing direct contact with the cornea. In some implementations, a row of staples may be deposited with substantially uniform distance between each staple. Accordingly, an effective seal may be achieved with reduced risk of dehiscence.

In some implementations, the stapling assembly may deposit proprietary bioabsorbable staples 610. For ptosis repair, a single, sterilized staple cartridge 600 may be used for each eye operated on. Thus, a staple cartridge used on a first patient eye may be removed from the forceps and exchanged with a second staple cartridge for use on a second eye of the patient.

It was identified that the Müller's muscle often regenerates within seven days. Accordingly, in some implementations the staples may comprise a mixture of FDA approved bio-absorbable polymers, for example, polylactic acid (PLA) and polyglycolic acid (PGA), to maintain structural integrity to facilitate natural wound healing for at least seven days and completely absorb into the tissue three weeks post-surgery. The PLA/PGA staples may be thermally cross-linked to retain mechanical strength comparable to titanium staples of similar geometry.

According to certain implementations, the forceps 400 may include millimeter markings 470 or other graduations on the grasping assembly or instrument body. For example, millimeter ruler markings may be laser-etched along the vertical axis of the forceps. Oculoplastic surgeons use a standard ratio of 1 mm of tissue resection to 2 mm of eyelid lift to determine the amount of excess Müller's muscle to resect. The graduations may help surgeons establish a precise determination of the amount of tissue to resect, in contrast to the conventional visual estimation and post-operative adjustment of the eyelid, if necessary. Accordingly, surgeons may operate with confidence and consistent results even when a patient suffers from differing degrees of ptosis in each eye.

According to certain implementations, the forceps 400 may further include a locking assembly 450A-B. The locking assembly may be operable to lock the grasping assembly in a closed position when engaged. In some implementations, the locking assembly may be disposed on the handle portion, as shown in FIG. 4. In an example implementation, the locking assembly may be engaged by sliding a hooked member on one arm into position to interlock with a notched member on the opposing arm. Other means of locking the forceps in a closed position will be apparent to one of skill in the art and are considered within the scope of this disclosure.

Figure 11:
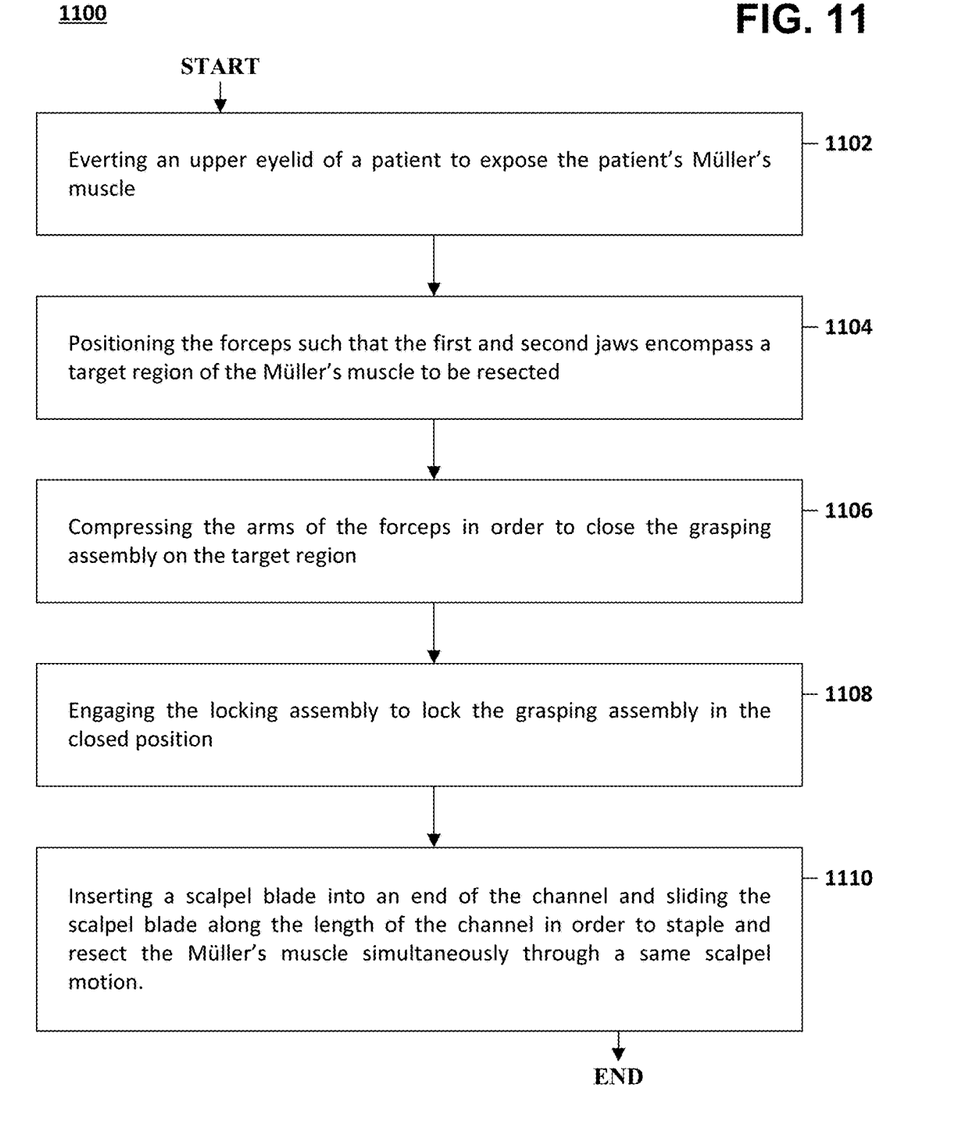
FIG. 11 is a flow diagram of a method 1100 for performing ptosis repair using the resecting and sealing forceps, according to an example implementation.

FIG. 11 is a flow diagram of a method 1100 for performing ptosis repair using the resecting and sealing forceps, according to an example implementation. As shown in FIG. 11, the method 1100 starts in block 1102, and, according to an example implementation, includes everting an upper eyelid of a patient to expose the patient's Müller's muscle. In block 1104, the method 1100 includes positioning the forceps such that the first and second jaws encompass a target region of the Müller's muscle to be resected. In block 1106, the method 1100 includes compressing the arms of the forceps in order to close the grasping assembly on the target region. In block 1108, the method 1100 includes engaging the locking assembly to lock the grasping assembly in the closed position. In block 1110, the method 1100 includes inserting a scalpel blade into an end of the channel and sliding the scalpel blade along the length of the channel in order to staple and resect the Müller's muscle simultaneously through a same scalpel motion.

It will be understood that the various steps shown in FIGS. 10 and 11 are illustrative only, and that steps may be removed, other steps may be used, or the order of steps may be modified.

Design Considerations

Based on discussions with several oculoplastic surgeons, performing extensive literature review, and observing internal ptosis repair surgery, the inventive team determined functional requirements for addressing unmet clinical needs.

A first critical function of the device is to guide resection of the Müller's muscle, thereby eliminating the risk of cutting the sutures holding the muscle together. A second critical function is sealing the tissue in a manner that provides uniform tissue compression. Additionally, the device may contain safety features to prevent misuse and reduce risk for both the patient and surgeon. Furthermore, the device should be comfortable to grip and use. Other design considerations include sterilization of the proposed device for first-time use (e.g., by ethylene oxide (EO) treatment or gamma radiation), and subsequent uses (e.g., by autoclave steam sterilization), and the inclusion of biologically compatible or absorbable materials to seal the Müller's muscle.

Specific performance metrics, engineering and design considerations, and constraints for the functional and customer requirements are detailed in the following sections. Metrics are also provided for customer satisfaction including potential timesavings as a result of the combination resecting and sealing device, the reduction in skill required to perform the Müllerectomy, and the improvement in the cosmetic outcome for the patient.

Performance Metrics

In order to design a device and procedure that both cuts and seals Müller's muscle to facilitate ptosis repair and improve patient outcomes, performance metrics for clamping, cutting, and sealing Müller's muscle were defined. These metrics were based on ISO standards, performance metrics of current medical devices, and scientific literature on various forms of transecting cutting and sealing tissue.

According to certain implementations, to ensure that the device is securely clamped on the Müller's muscle 320 before the surgeon cuts and seals, the force required to close the device on tissue may be 5 $lb_f \pm 3$ $lb_f$ as determined by a Finite Element Analysis (FEA) simulation on the conventional Putterman clamp 200, as shown in FIG. 2. The device may also include a safety feature that prevents the user from unintentionally cutting before sealing the tissue. Additionally, a separate locking mechanism 450A-B may fix the jaws 461A-B of the device onto Müller's muscle. In order to prevent tearing or accidental release of Müller's muscle while cutting and sealing, a force required to pull the tissue out of the jaws of the device while it is locked may be no less than 10 $lb_f$. This force value may be at least two times greater than the clamp force to ensure that the user cannot easily remove the tissue while the device is in the locked position while minimizing tissue trauma.

In some implementations, the force required to seal the tissue may be no greater than 3 $lb_f$ in order to ensure a seal which is both secure and at least functionally equivalent to the conventional clamping technique. Additionally, the sealing agent may be bio-absorbable (per ISO 10993) and, in an example implementation, designed to absorb completely in three weeks. The sealing agent may be evenly spaced throughout the length of the jaws 461A-B of the device in order to provide a uniform seal of the fine tissue.

In some implementations, to provide a complete and precise transection of Müller's muscle, a force required to cut the excess Müller's muscle with the proposed device should be suitable for cutting the muscle with the 15-scalpel 300 while avoiding damaging the muscle unnecessarily. Based on force values found in literature, the force required to cut the muscle may not exceed 3 $lb_f$. Moreover, the time required to transect the muscle may be 3 seconds plus or minus 3 seconds. The blade responsible for cutting the tissue in the device may be durable enough to transect Müller's muscle quickly, effectively, and with low force for a minimum of twelve transections.

From a human factors, ergonomics, and usability standpoint, it is beneficial if the device fits within the surgeon's fingers and is easy to hold, and functions within the surgeon's dexterity limits without causing fatigue. Thus, in some implementations, the distance at the points of contact between the fingers and the device may not exceed 4 cm based on the minimum fifth-percentile maximum grip diameters for individuals without dexterity disabilities. Moreover, in order to ensure that the device fits within the surgeon's hand, critical device features including any locking mechanisms and the cutting and sealing mechanism may be accessible within a distance less than 10 cm, which is well below the minimum fifth-percentile hand width for males and females. In addition to these size considerations, the device may not weigh more than 3 pounds based on the maximum coupling capacity for precision of the muscles in the hands and forearm. These features are intended to mitigate or eliminate surgeon muscle fatigue resulting from use of the device.

In some implementations, since the device may interact with human tissue including the muscles of the eyelid, virtually all components of the device may need to be made of biologically biocompatible materials per ISO 10993, in order to reduce the risk of infection and inflammation. The device may have features that enable the surgeon to visualize the tissue that is being clamped in order to facilitate uniform tissue compression and visibility. In order to protect both the patient and the surgeon, the device may lack any sharp or rough surfaces that would cause rips or tears in the surgeon's gloves.

Since an intended use of the device is within a sterile operating environment, in some implementations, the device and all of its components may be sterile when packaged and shipped to the operating site. Packaging may be minimized in order to reduce waste. The device may have a shelf life of a minimum of three years as per ASTM F1980-02 and the FDA Shelf Life of Medical Devices Recommendation. Per FDA 21 CFR 801, the device may be stored at room temperature with minimal humidity and be labeled as a prescription medical device, indicating the intended use, product, and manufacturer information.

Constraints

Two main constraints identified for the device include the anatomical characteristics of the eye region and the cost to the health-care provider, the latter ultimately relating to device reusability. In terms of anatomical size constraints, the jaws of the device may be large enough to enclose all of the muscle to be resected, yet be small enough not to extend past the eyelid. To prevent interference with the eye, nose, eyebrow, and forehead, in some implementations, the length of the jaws of the device may not exceed 3 cm. In addition to the length of the jaws of the device, the width of the jaws may not exceed 0.76 cm since the distance between the top of the eye and the eyebrow is around 1.143 cm on average.

Since the conventional Putterman clamp 200 may be currently reused in up to 500 procedures, in some implementations, the resecting and sealing device may withstand 500 autoclave steam sterilization cycles. Since autoclave steam sterilization uses extremely high temperatures and pressures, the device may be made exclusively from materials that can resist high temperature and pressure without losing functionality, yielding, or deforming. Some such materials are outlined in ISO 17665-01:2006 and include metals such as titanium or stainless steel, or plastics like ultem. Another design requirement related to autoclave steam sterilization is that the device may be designed to fit within an autoclave sterilization tray or have its own custom sterilization tray designed if it is taller than two inches. The device may alternatively be designed for single-patient use or fully disposable device after a single procedure.

Experimental Results

Figure 9:
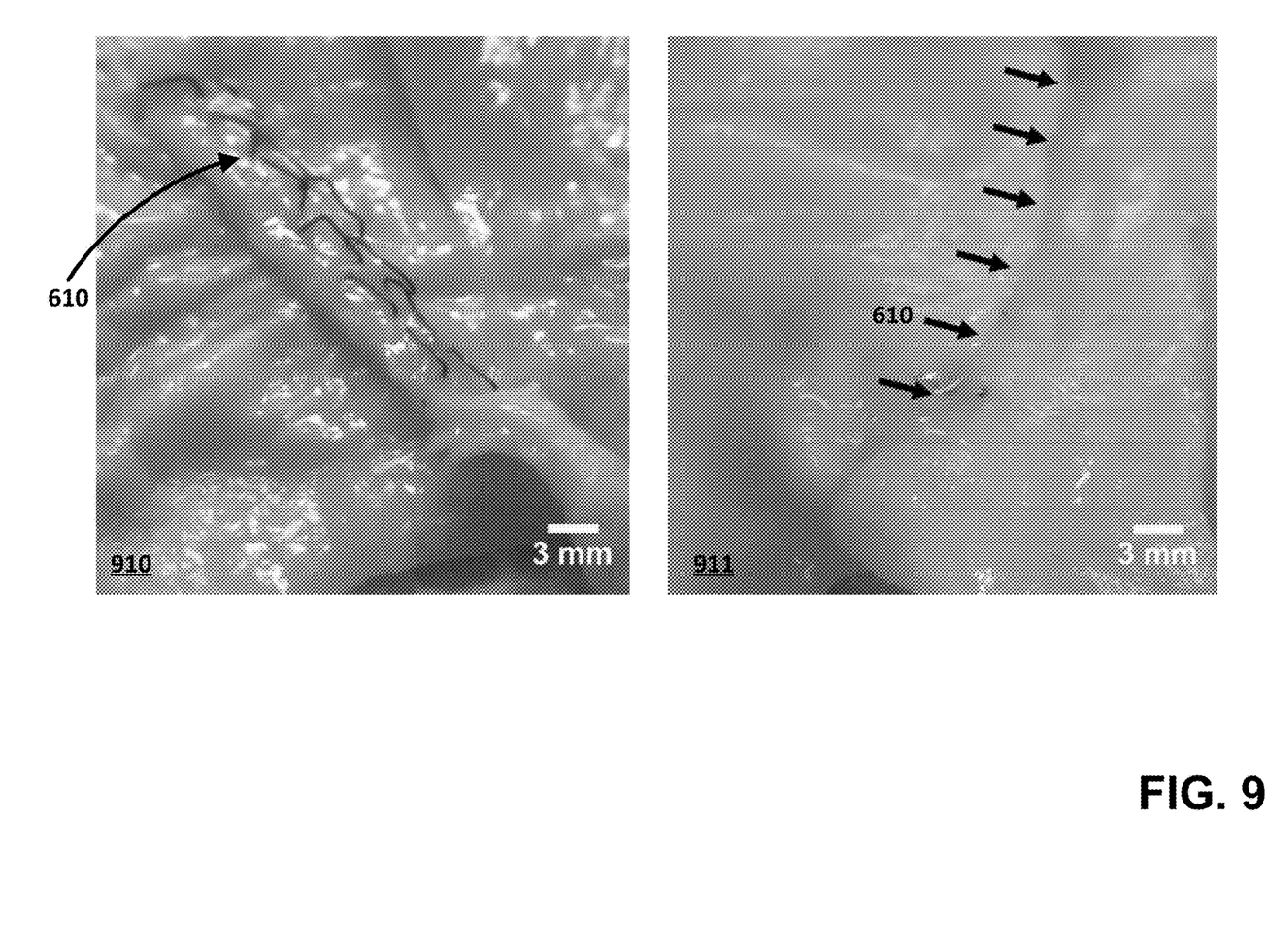
FIG. 9 depicts photos 910 and 911 of test tissue sealed with staples 610, according to an example implementation.

FIG. 9 depicts photos 910 and 911 of test tissue sealed with staples 610, according to an example implementation. As a proof-of-concept, the efficacy of staple formation and tissue closure was demonstrated on chicken skin—a close model of the mechanical properties of human eyelid tissue. The resulting tissue from these studies demonstrated the sealed incision is smooth and secure. Using proof-of-concept forceps, the chicken skin was resected and sealed in 2-4 minutes, which is a conservative 73% reduction in surgical time over the conventional procedure. The prototype of this resecting and sealing forceps was machined from aluminum, and was analogous to forceps 400 in FIG. 4. Other forceps embodying then invention can also be utilized, such as, for example, the forceps of FIG. 8. Forceps can be made from any typical medical-grade material.

Several prototype staple cartridges have also been prepared, including a cartridge 3D-printed from ABS and a cartridge machined from aluminum. The staples can be made from any typical medical-grade material, including aluminum or bioabsorbable materials such as PLA, PGA, PLGA, and mixtures thereof. In some implementations, the millimeter-scale bioabsorbable staples might comprise of a mixture of PLA and PGA and made using micro-molding followed by a thermally-induced polymer cross-linking process.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and also to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A forcipate surgical instrument comprising:
   an instrument body having a proximal end, an intermediate handle portion, and a working portion at a distal end, the instrument body comprising first and second mutually opposed elongate arms;
   a grasping assembly; and
   a mechanical locking assembly operable to lock the grasping assembly in a closed position when engaged;
   wherein the arms of the instrument body are hingedly secured together at the proximal end and compressible towards each other and decompressible away from each other to respectively close and open the grasping assembly at the distal end;
   wherein the grasping assembly has first and second elongate jaws, each jaw extending from a respective arm at the distal end and being disposed substantially orthogonal to the handle portion, the jaws being adapted to grasp tissue therebetween when the arms are compressed;
   wherein the grasping assembly is adapted to receive a scalpel blade slid along a channel running lengthwise through at least one of the first and second jaws, in order to cut tissue grasped therebetween when the grasping assembly is in a closed position; and
   wherein the mechanical locking assembly comprises a notched member disposed on one of the first and second arms and a corresponding hooked member shaped and dimensioned to interlock with the notched member, the locking assembly adapted to activate by sliding the hooked member into position to engage the notched member when the grasping assembly is in the closed position.

2. A method of performing ptosis surgery using the forcipate surgical instrument of claim 1 comprising:
   everting an upper eyelid of a patient to expose the patient's Müller's muscle;
   positioning the forcipate surgical instrument such that the first and second jaws encompass a target region of the Müller's muscle to be resected;
   compressing the arms of the forcipate surgical instrument in order to close the grasping assembly on the target region;
   sealing the patient's Müller's muscle below the forcipate surgical instrument with a sealing agent; and
   inserting a scalpel blade into an end of the channel and sliding the scalpel blade along the length of the channel in order to resect the target region, wherein the scalpel blade is prevented from cutting the sealing agent by the channel.

3. The forcipate surgical instrument of claim 1, wherein the grasping assembly comprises a stapling assembly secured to at least one of the first and second jaws.

4. The forcipate surgical instrument of claim 3, wherein the stapling assembly comprises a cartridge adapted to deposit staples into the tissue grasped between the first and second jaws, the staples being deposited in one or more rows substantially parallel to the channel and on a side of the channel opposite the handle portion.

5. The forcipate surgical instrument of claim 4, wherein the stapling assembly further comprises a plurality of micro-anvils displaced on a jaw of the first and second jaws opposite the cartridge, the micro-anvils adapted to form the staples into the tissue.

6. The forcipate surgical instrument of claim 4, wherein the one or more rows of staples are deposited into the tissue with a substantially uniform distance between each staple.

7. The forcipate surgical instrument of claim 4, wherein the staples comprise bio-compatible staples.

8. The forcipate surgical instrument of claim 7, wherein the bio-compatible staples are bioabsorbable.

9. The forcipate surgical instrument of claim 4, wherein the cartridge is detachable from the stapling assembly and interchangeable for another cartridge.

10. The forcipate surgical instrument of claim 3, wherein the stapling assembly is adapted to receive the scalpel blade through the channel and to deposit the staples into the tissue grasped between the first and second jaws when the scalpel blade is slid along the channel, in order that the tissue may be cut and stapled simultaneously through a same scalpel motion.

11. The forcipate surgical instrument of claim 10, wherein the stapling assembly comprises a scalpel-driven mechanism slideable along a length of the stapling assembly by the scalpel blade to drive the deposit of the staples into the tissue when the scalpel blade is being slid along the channel.

12. The forcipate surgical instrument of claim 11, wherein the instrument body comprises linear graduations to aid determination of a target region of the tissue.

13. A method of performing ptosis surgery using the forcipate surgical instrument of claim 10 comprising:
   everting an upper eyelid of a patient to expose the patient's Müller's muscle;

positioning the forcipate surgical instrument such that the first and second jaws encompass a target region of the Müller's muscle to be resected;

compressing the arms of the forcipate surgical instrument in order to close the grasping assembly on the target region;

engaging the locking assembly to lock the grasping assembly in the closed position; and inserting a scalpel blade into an end of the channel and sliding the scalpel blade along the length of the channel in order to staple and resect the Müller's muscle through the same motion.

14. The forcipate surgical forceps instrument of claim 1 further comprising a hinged portion opposite the handle portion from the working portion.

15. The forcipate surgical instrument of claim 1 further comprising a hinged portion between the handle portions and the working portion.

16. A method of performing ptosis surgery using a forcipate surgical instrument comprising an instrument body having a proximal end, an intermediate handle portion, and a working portion at a distal end, the instrument body comprising first and second mutually opposed elongate arms, the arms being hingedly secured together at the proximal end and being compressible towards each other and decompressible away from each other to respectively close and open a grasping assembly at the distal end, the grasping assembly having first and second elongate jaws, each jaw extending from a respective arm at the distal end and being disposed substantially orthogonal to the handle portion, the jaws being adapted to grasp tissue therebetween when the arms are compressed, and the grasping assembly being adapted to receive a scalpel blade slid along a channel running lengthwise through at least one of the first and second jaws, in order to cut tissue grasped therebetween when the grasping assembly is in a closed position, the method comprising:

everting an upper eyelid of a patient to expose the patient's Müller's muscle;

positioning the forcipate surgical instrument such that the first and second jaws encompass a target region of the Müller's muscle to be resected;

compressing the arms of the forcipate surgical instrument in order to close the grasping assembly on the target region;

sealing the patient's Müller's muscle below the forcipate surgical instrument with a sealing agent; and inserting a scalpel blade into an end of the channel and sliding the scalpel blade along the length of the channel in order to resect the target region, wherein the scalpel blade is prevented from cutting the sealing agent by the channel.

* * * * *